United States Patent
Wright et al.

(10) Patent No.: US 9,295,812 B2
(45) Date of Patent: Mar. 29, 2016

(54) VARIABLE STIFFNESS GUIDEWIRE SYSTEMS AND METHODS

(75) Inventors: Jay Ralph Wright, Temecula, CA (US); Samuel Seunghae Ahn, Dallas, TX (US); Mark Philip Ashby, Laguna Niguel, CA (US)

(73) Assignee: Wright-Ahn Technologies, LLC, Los Angeles, CA (US)

( * ) Notice: Subject to any disclaimer, the term of this patent is extended or adjusted under 35 U.S.C. 154(b) by 781 days.

(21) Appl. No.: 13/193,499

(22) Filed: Jul. 28, 2011

(65) Prior Publication Data
US 2013/0030362 A1    Jan. 31, 2013

(51) Int. Cl.
*A61M 25/09* (2006.01)

(52) U.S. Cl.
CPC .......... *A61M 25/09* (2013.01); *A61M 25/09033* (2013.01); *A61M 2025/0915* (2013.01); *A61M 2025/09083* (2013.01); *A61M 2025/09116* (2013.01)

(58) Field of Classification Search
CPC ........... A61M 2025/0915; A61M 2025/09083; A61M 2025/09116; A61M 25/09; A61M 25/09033
USPC ........................................................ 604/525
See application file for complete search history.

(56) References Cited

U.S. PATENT DOCUMENTS

| | | |
|---|---|---|
| 777,191 A | 12/1904 | Engle |
| 3,521,620 A | 7/1970 | Cook |
| 3,600,014 A | 8/1971 | Harris |
| 4,215,703 A | 8/1980 | Willson |
| 4,456,017 A | 6/1984 | Miles |
| 4,799,496 A | 1/1989 | Hargreaves et al. |
| 4,886,067 A | 12/1989 | Palermo |
| 5,163,947 A | 11/1992 | Kvalo et al. |
| 5,303,714 A | 4/1994 | Abele et al. |
| 5,573,010 A | 11/1996 | Pflugbeil |
| 5,605,162 A * | 2/1997 | Mirzaee et al. ............... 600/585 |
| 5,762,615 A | 6/1998 | Weier |
| 5,772,609 A | 6/1998 | Nguyen et al. |
| 5,800,421 A | 9/1998 | Lemelson |
| 5,845,646 A | 12/1998 | Lemelson |
| 5,931,819 A | 8/1999 | Fariabi |
| 5,957,903 A | 9/1999 | Mirzaee et al. |
| 6,058,323 A | 5/2000 | Lemelson |
| 6,090,139 A | 7/2000 | Lemelson |
| 6,096,023 A | 8/2000 | Lemelson |
| 6,139,511 A | 10/2000 | Huter et al. |
| 6,233,474 B1 | 5/2001 | Lemelson |
| 6,286,514 B1 | 9/2001 | Lemelson |

(Continued)

FOREIGN PATENT DOCUMENTS

WO    WO 2004/002310 A1    1/2004
WO       2013/016709         1/2013

OTHER PUBLICATIONS

Office Action in U.S. Appl. No. 12/192,946, mailed Dec. 10, 2010.

(Continued)

*Primary Examiner* — Laura Bouchelle
(74) *Attorney, Agent, or Firm* — Nixon Peabody LLP

(57) ABSTRACT

Guidewires, actuators and methods of using the guidewires and actuators are described. These tools and methods allow a user to select and maintain different guidewire stiffness characteristics such that a single guidewire can address a range of access capabilities.

15 Claims, 11 Drawing Sheets

(56) References Cited

U.S. PATENT DOCUMENTS

| | | |
|---|---|---|
| 6,287,292 B1 | 9/2001 | Fariabi |
| 6,287,294 B1 | 9/2001 | Lemelson |
| 6,293,282 B1 | 9/2001 | Lemelson |
| 6,321,106 B1 | 11/2001 | Lemelson |
| 6,327,492 B1 | 12/2001 | Lemelson |
| 6,394,997 B1 | 5/2002 | Lemelson |
| 6,400,980 B1 | 6/2002 | Lemelson |
| 6,401,988 B1 | 6/2002 | Parent et al. |
| 6,468,203 B2 | 10/2002 | Belson |
| 6,491,663 B1 | 12/2002 | Lemelson |
| 6,514,237 B1 | 2/2003 | Maseda |
| 6,524,301 B1 | 2/2003 | Wilson et al. |
| 6,532,387 B1 | 3/2003 | Marchitto et al. |
| 6,562,021 B1 | 5/2003 | Derbin et al. |
| 6,610,007 B2 | 8/2003 | Belson et al. |
| 6,632,215 B1 | 10/2003 | Lemelson |
| 6,638,266 B2 | 10/2003 | Wilson et al. |
| 6,679,836 B2 | 1/2004 | Couvillon, Jr. |
| 6,770,027 B2 | 8/2004 | Banik et al. |
| 6,869,396 B2 | 3/2005 | Belson |
| 6,890,297 B2 | 5/2005 | Belson |
| 6,969,395 B2 | 11/2005 | Eskuri |
| 7,018,346 B2 * | 3/2006 | Griffin et al. ............. 600/585 |
| 7,020,516 B2 | 3/2006 | Flock et al. |
| 7,044,907 B2 | 5/2006 | Belson |
| 7,547,288 B2 | 6/2009 | Murayama et al. |
| 7,878,984 B2 | 2/2011 | Jacobsen et al. |
| 8,100,838 B2 | 1/2012 | Wright et al. |
| 8,376,963 B2 | 2/2013 | Wright et al. |
| 2003/0065373 A1 | 4/2003 | Lovett et al. |
| 2003/0069521 A1 | 4/2003 | Reynolds et al. |
| 2003/0127786 A1 | 7/2003 | Daily et al. |
| 2004/0112454 A1 | 6/2004 | Takagi |
| 2006/0047303 A1 | 3/2006 | Ortiz et al. |
| 2006/0224175 A1 | 10/2006 | Vrba |
| 2009/0131831 A1 | 5/2009 | Wright et al. |
| 2009/0131911 A1 | 5/2009 | Wright et al. |
| 2009/0131912 A1 | 5/2009 | Wright et al. |
| 2009/0254001 A1 | 10/2009 | Wright et al. |
| 2010/0249656 A1 | 9/2010 | Wright et al. |
| 2011/0144538 A1 * | 6/2011 | Shimogami et al. .......... 600/585 |
| 2012/0123390 A1 | 5/2012 | Wright et al. |
| 2013/0158516 A1 | 6/2013 | Wright et al. |

OTHER PUBLICATIONS

Office Action in U.S. Appl. No. 12/192,946, mailed Jun. 20, 2011.
Office Action in U.S. Appl. No. 12/192,950, mailed Feb. 24, 2011.
Office Action in U.S. Appl. No. 12/192,950, mailed Jul. 12, 2011.
Office Action in U.S. Appl. No. 12/192,958, mailed Mar. 30, 2011.
Office Action in U.S. Appl. No. 12/192,958, mailed Aug. 31, 2011.
Office Action in U.S. Appl. No. 12/192,958, mailed Mar. 15, 2012.
Office Action in U.S. Appl. No. 12/415,919, mailed May 31, 2011.
Office Action in U.S. Appl. No. 12/415,919, mailed Oct. 12, 2011.
Office Action in U.S. Appl. No. 12/797,101, mailed Feb. 8, 2012.
Notice of Allowance in U.S. Appl. No. 12/797,101, mailed Oct. 11, 2012.
Office Action in U.S. Appl. No. 12/192,958, mailed Dec. 18, 2012.
Office Action in U.S. Appl. No. 13/355,448, mailed Mar. 26, 2013.
Office Action in U.S. Appl. No. 12/415,919, mailed Mar. 29, 2013.
International Search Report and Written Opinion in International Application No. PCT/US2012/048723, mailed Feb. 28, 2013.
Notice of Allowance in U.S. Appl. No. 12/192,946, mailed Nov. 4, 2011.
Office Action in U.S. Appl. No. 12/415,919, mailed Apr. 23, 2012.
Office Action in U.S. Appl. No. 12/192,950, mailed May 9, 2013.
Office Action in U.S. Appl. No. 12/415,919, mailed Oct. 8, 2013.
Office Action in U.S. Appl. No. 12/415,919, mailed Aug. 14, 2014.
Office Action in U.S. Appl. No. 13/770,918, mailed Jul. 1, 2013.
Office Action in U.S. Appl. No. 12/415,919, mailed Jan. 31, 2011.
Advisory Action in U.S. Appl. No. 12/415,919, mailed Jul. 25, 2013.
International Preliminary Report on Patentability in International Application No. PCT/US2012/048723, mailed Feb. 6, 2014.
Office Action in U.S. Appl. No. 12/415,919, mailed Aug. Sep. 10, 2015.

* cited by examiner

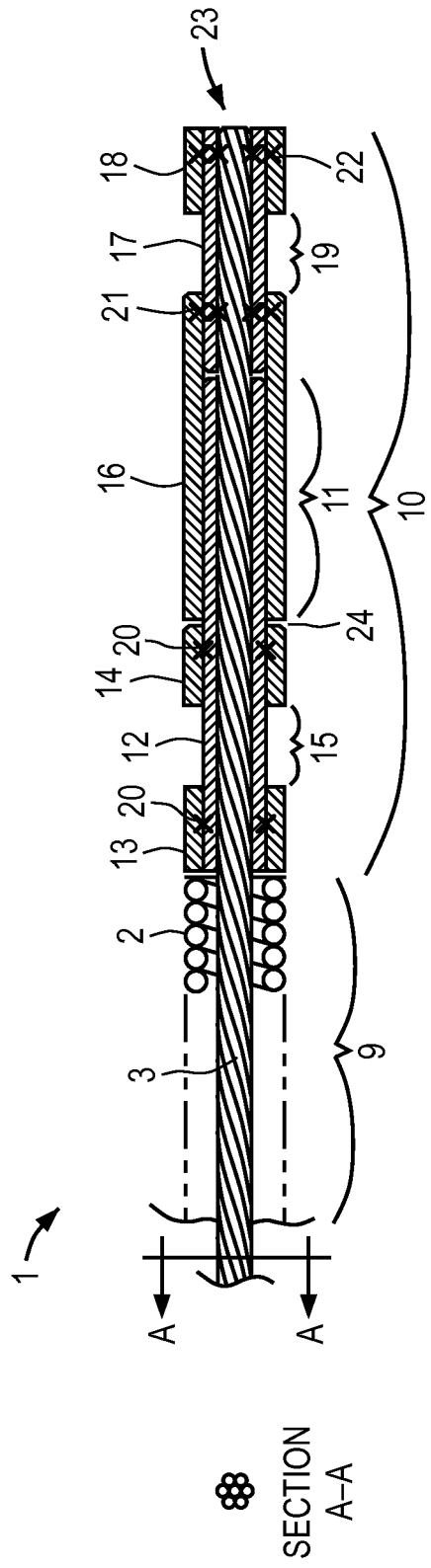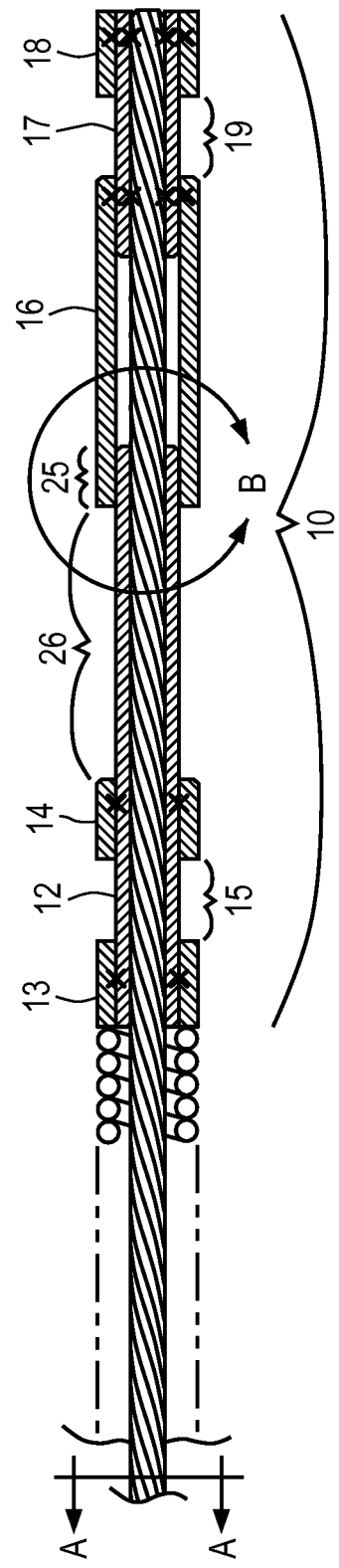

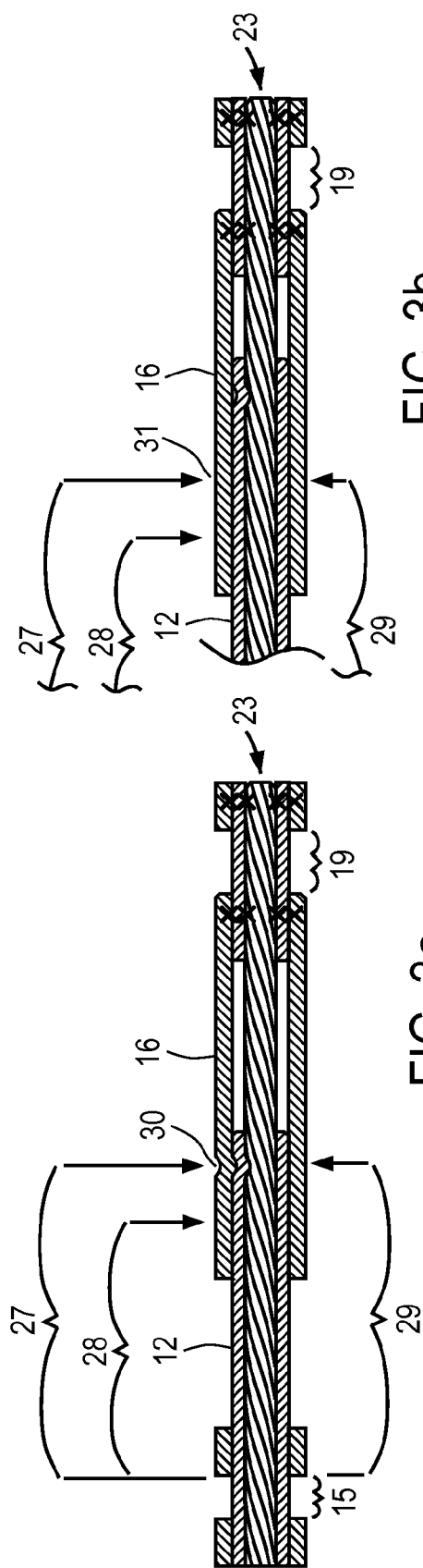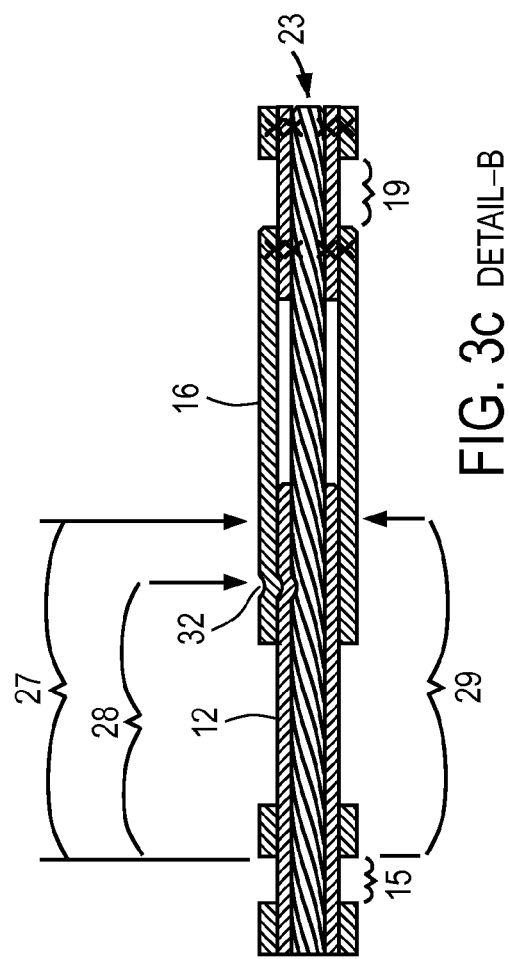

VARIABLE STIFFNESS GUIDEWIRE SYSTEMS AND METHODS

BACKGROUND

1. Field

The subject invention relates to variable stiffness guidewire systems and methods.

2. Related Art

Guidewires of different stiffness characteristics provide users with a range of capabilities to gain and maintain access during diagnostic and interventional procedures. The capabilities required are dependent on variables including, but not limited to, patient anatomy, placement target, tools to be placed, and physician preference. Accordingly, it is commonplace and often necessary to perform one or more guidewire exchanges during these procedures.

While guidewire exchanges are well accepted, they are time consuming and burdened by the cost of the additional guidewires. Thus, there is a need to reduce or eliminate the need for guidewire exchanges to reduce procedure time and cost.

SUMMARY

The following summary of the invention is included in order to provide a basic understanding of some aspects and features of the invention. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below.

According to an aspect of the invention, a system is provided that includes a variable stiffness guidewire comprising a guidewire body, the guidewire body having a proximal end and a distal end; an actuator interface at the proximal end of the guidewire body and comprising an inner canister and an outer canister at least partially telescoping relative to one another; a tension cable coupled to the outer canister and coupled to the distal end of the guidewire body, the tension cable movable within the inner canister; and an actuator couplable to the actuator interface and configured to move the outer canister relative to the inner canister to vary the stiffness of the guidewire.

The actuator interface may be configured to increase the stiffness of the guidewire. The actuator interface is configured to decrease stiffness of the guidewire. The stiffness is adjusted by moving the outer canister distally relative to the inner canister.

The actuator may include a crimper configured to maintain the stiffness of the guidewire body at the desired stiffness. The actuator interface may circumferentially clamp the guidewire to maintain the desired stiffness.

The guidewire may include a tip coil and a body coil, and the tip coil may be more flexible than the body coil.

The actuator may include an actuator body and an actuator slide, the actuator slide movable relative to the actuator body to adjust the stiffness of the guidewire via the actuator interface. The actuator may include a tension knob coupled to a tension screw. The actuator may include markings to identify an amount of stiffness of the guidewire.

According to another aspect of the invention, an actuator is provided for adjusting the stiffness of a variable stiffness guidewire that includes an actuator body; an actuator slide movable relative to the actuator body; and a crimping tool coupled to the actuator slide. The crimping tool may include a tension knob coupled to a tension screw.

According to a further aspect of the invention, a system is provided that includes means for positioning a guidewire in a body passage of a patient; means for adjusting the stiffness of the guidewire in the body passage; and means for maintaining the stiffness of the guidewire in the body passage. The means for adjusting the stiffness of the guidewire may include means for increasing and decreasing the stiffness of the guidewire.

According to yet another aspect of the invention, a variable stiffness guidewire is provided that includes a guidewire body, the guidewire body having a proximal end and a distal end; an actuator interface at the proximal end of the guidewire body and comprising an inner canister and an outer canister at least partially telescoping relative to one another; and a tension cable coupled to the outer canister, coupled to the distal end of the guidewire body and movable within the inner canister.

The actuator interface may be configured to increase the stiffness of the guidewire. The actuator interface may be configured to decrease stiffness of the guidewire. The actuator interface may include a crimper configured to maintain the stiffness of the guidewire body at the desired stiffness. The stiffness may be adjusted by moving the outer canister distally relative to the inner canister.

The guidewire body may include a tip coil and a body coil, and the tip coil may be more flexible than the body coil.

The actuator interface may circumferentially clamp the guidewire body to maintain the desired stiffness.

According to another aspect of the invention, a variable stiffness guidewire is provided that includes a guidewire body, the guidewire body having a proximal end and a distal end; a floppy tip having a proximal end and a distal end, the proximal end of the floppy tip coupled to the distal end of the guidewire body, the flexibility of the floppy tip being greater at the distal end of the floppy tip than at the proximal end of floppy tip; and a tension cable coupled to the actuator interface and coupled to the floppy tip.

The guidewire may further include an actuation interface at the proximal end of the guidewire body, the tension cable coupled to the actuation interface.

The floppy tip may include a plurality of strands and the number of strands at the proximal end may be greater than the number of strands at the distal end.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 1 is a cross-sectional view of a proximal end of a guidewire in accordance with one embodiment of the invention;

FIG. 2 is a cross-sectional view of the proximal end of the guidewire in accordance with one embodiment of the invention;

FIGS. 3A-3C are cross-sectional views of the proximal end of the guidewire in accordance with one embodiment of the invention;

DETAILED DESCRIPTION

Figure 4:
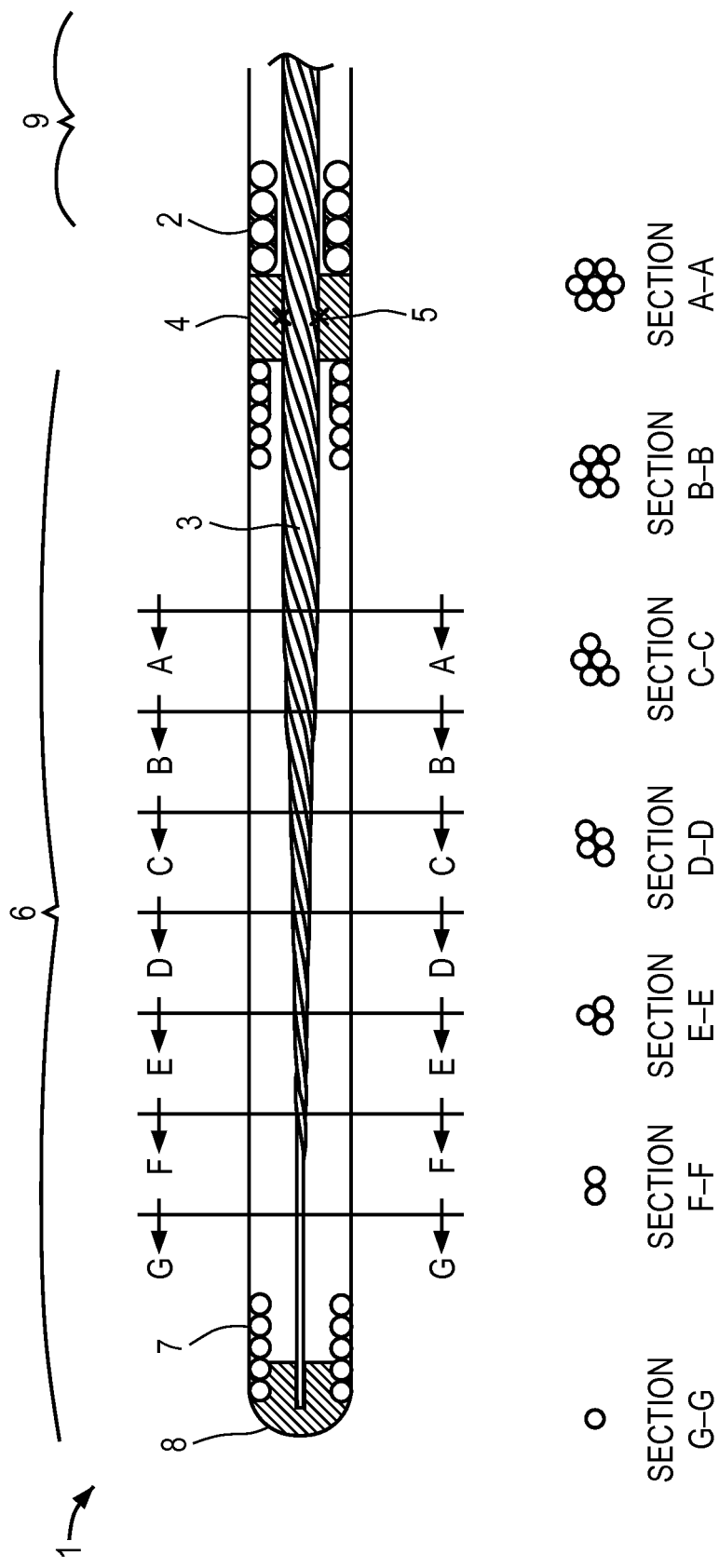
FIG. 4 is a cross-sectional view of a distal end of a guidewire in accordance with one embodiment of the invention.

Disclosed herein are guidewires, actuators, and methods of using the guidewires and actuators that allow a user to select and maintain different guidewire stiffness characteristics such that a single guidewire can address a range of access capabilities currently requiring multiple guidewires.

An embodiment of the invention will now be described in detail with reference to FIG. 1. FIG. 1 shows the proximal region of a guidewire 1 according to one embodiment of the invention. The guidewire 1 includes a guidewire body 9. Guidewire 1 may be or include features similar to the guidewires described in co-pending application Ser. Nos. 12/192,946 and 12/192,950, both titled "Variable Stiffness Guidewire Systems" and both filed on Aug. 15, 2008, the entireties of which are hereby incorporated by reference.

The proximal region of guidewire 1 shown in FIG. 1 also includes an actuation interface 10 positioned at a proximal end of the guidewire body 9. The actuation interface 10 is configured to adjust and maintain the stiffness of the guidewire body 9. The position of the actuation interface 10 shown in FIG. 1 represents a minimum guidewire stiffness. As will be described in further detail, an actuator is couplable to the actuation interface 10 to adjust and maintain the stiffness.

The actuation interface 10 includes an inner canister 12 and an outer canister 16 that mate telescopically. The inner canister 12 and outer canister 16 are slideable telescopically over at least part of their length 11 to adjust the stiffness of the guidewire body 9.

A tension cable 3 extends within the guidewire body 9 from the actuation interface 10 and is coupled at its distal end with a tip of the guidewire body at the distal end of the guidewire body 9. The tension cable 3 is coupled at its proximal end with the actuator interface 10. The tension cable 3 moves with little or no friction inside the inner canister 12.

The actuator interface 10 also includes rings 13 and 14. Inner canister 12 and rings 13 and 14 form forward actuator land 15. Rings 13 and 14 can be formed as part of the inner canister 12 such as by machining, molding, sintering, casting, or any other suitable techniques. In FIG. 1, the rings 13 and 14 are illustrated as hypotube segments having inner and outer diameters similar to the outer canister 16 that are fixed to the inner canister 12 at fixation points 5. The fixation at fixation points 5 may be, for example, mechanical, such as by crimping, or other know techniques.

The actuation interface 10 also includes an inner stem 17 and a ring 18. The proximal end of the tension cable 3 is coupled with the ring 18. Outer canister 16, inner stem 17, and ring 18 form the rearward actuator land 19. Inner stem 17 and ring 18 can be formed as part of the outer canister 16 such as by machining, molding, sintering, casting, or any other suitable techniques. In FIG. 1, the inner stem 17 and ring 18 are illustrated as hypotube segments.

The inner stem 17 is fixed to the outer canister 16 and tension cable 3 at fixation point 21, and is fixed to the proximal ring 18 and tension cable 3 as fixation point 22 at the proximal end 23 of the guidewire 1. Inner stem 17 typically has inner and outer diameters similar to the inner canister 12. Ring 18 typically has inner and outer diameters similar to the outer canister 16. Fixation 21 and 22 may be, for example, mechanical, such as by crimping, or other know techniques.

As explained above, in FIG. 1, the relative position of the inner canister 12 and outer canister 16 corresponds to a minimum guidewire stiffness. In this position, there is no tensile force on the tension cable 3 and the distance 24 between the outer canister 16 and ring 14 is zero. Alternatively, the distance 24 between the inner canister 12 and inner stem 17 can be zero.

FIG. 2 shows the actuation interface 10 in a position representing an increased guidewire stiffness (i.e., increased relative to the minimum guidewire stiffness position shown in FIG. 1). The distance 26 between the outer canister 16 and ring 14 is the sum of the axial elongation of the tension cable 3 and the axial compression of the body coil 2 corresponding to the force applied to achieve maximum guidewire stiffness. In FIG. 2, the inner canister 12 and outer canister 16 mate telescopically over a reduced length 25 (i.e., a reduced length relative to FIG. 1).

It will be appreciated that any desired guidewire stiffness between the minimum stiffness shown in FIG. 1 and the maximum distance shown in FIG. 2 can be achieved by selecting the distance between the outer canister 16 and ring 14 so that it is greater than distance 24 but less than distance 26. It will be appreciated that the distance may be any value or range of values between distance 24 and distance 26. In one embodiment, distance 24 is any value or range of values between about 1 mm and about 50 mm distance 26 is any value or range of values between about 5 mm and about 5 cm. It will be appreciated that distance 24 may also be less than 1 mm or greater than 50 mm and distance 26 may be less than 5 mm or greater than 5 cm.

FIGS. 3A, 3B, and 3C illustrate embodiments for maintaining a desired stiffness of the guidewire using the actuation interface 10 in accordance with one embodiment of the invention. Locations 27, 28 and 29 are positions for crimping the guidewire relative to the forward land 15 of guidewire 1. The crimp tool resides within an actuator, which will be described in further detail hereinafter.

FIG. 3A shows the actuation interface 10 set to maintain maximum guidewire stiffness. The actuation interface 10 is first positioned at the distance 26 between the outer canister 16 and ring 14. A crimping tool is then positioned at location 27 to create deformation 30 within telescopically mating length 25. The deformation 30 is sufficient to maintain the distance 26 even against the high forces of the tension cable 3 at maximum guidewire stiffness trying to pull the outer canister 16 distally.

As shown in FIG. 3B, the actuation interface 10 applies additional force in the distal direction to the outer canister (using an actuator as described above). The tension cable force plus the additional force from the actuator are sufficient to overcome deformation 30, causing it to yield as indicated by reference number 31. This allows a distal movement of the outer canister 10 to provide a desired reduction in guidewire stiffness back down to minimum stiffness at distance 24. The actuation interface 10 can therefore be used to set, maintain, and release any guidewire stiffness between the minimum and maximum.

It will be appreciated that repeated use of a previously used crimp location to maintain guidewire stiffness is possible until the materials in that crimp location of the outer canister 16 and/or inner canister 12 are fatigued beyond their capacity to resist the force applied to the tension cable 3. If this occurs, or at the users preference, an alternate crimp location 28, located axially of location 27, can be used as shown in FIG. 3C to create deformation 32. Alternatively, an alternate crimp location 29, located radially of location 27, can be used. It will be appreciated that these features allow for an infinite selection of stiffness to be maintained, and numerous cycles of stiffness application, release, and reapplication.

FIG. 4 shows the distal region of guidewire 1 according to one embodiment of the invention. The guidewire 1 includes a body coil 2, a tension cable 3 and a floppy tip 6. Guidewire 1 may be or include features similar to the guidewires described in co-pending application Ser. Nos. 12/192,946 and 12/192,950, both titled "Variable Stiffness Guidewire Systems" and both filed on Aug. 15, 2008, the entireties of which are hereby incorporated by reference.

The distal end of the body coil 2 is terminated by a distal cable bushing 4 fixed to the tension cable 3 at fixation point 5, by, for example, crimping or other mechanical means. In one embodiment, the fixation point 5 is about 10 cm to 30 cm, and, in one particular embodiment, the fixation point 5 is about 10 cm-20 cm, adjacent the distal end of the tension cable 3.

The segment of the tension cable 3 that extends distally of the distal cable bushing 4 is the core of the floppy tip 6. The floppy tip 6 includes a tip coil 7 and is terminated at its distal end by a bushing such as cable bushing 4, adhesive or solder 8, or other suitable means.

The floppy tip 6 may be more flexible than the body 9 of the guidewire 1. Accordingly, the tip coil 7 has equal or greater flexibility than the body coil 2. In one embodiment, the floppy tip 6 is progressively more flexible moving distally. This may be accomplished by removing strand elements of the tension cable 3 within the floppy tip region, such that the number of cable strands reduces by one or more than one strands, moving from the proximal region of the floppy tip 6 to the distal region of the floppy tip.

In one embodiment, to construct a 0.035 inch diameter guidewire, a 0.035 inch diameter body coil 2 and tip coil 7 are used. Individual strands are removed from a 0.018 inch diameter tension cable 3 comprised of seven individual 0.006 inch SST strands, such that beginning at the tip coil 7 adjacent a 0.035 inch diameter distal cable bushing 4 and moving distally, the strand count goes from 7 (section A-A) to 6 (section B-B), moving further distally the strand count goes from 6 to 5 (section C-C), moving further distally the strand count goes from 5 to 4 (section D-D), moving further distally the strand count goes from 4 to 3 (section E-E), moving further distally the strand count goes from 3 to 2 (section F-F), moving further distally the strand count goes from 2 to 1 (section G-G). It will be appreciated that the above embodiment is merely exemplary and that the variation in flexibility may occur in a manner different than that described above. For example, the total number of strands may be less than seven or greater than seven, and may be any value or range of values between about two strands and about 50 strands. In another example, the number of points in which strands are removed may be less than or greater than described above (i.e., any value or range of values between one transition point and about 50 transition points). In yet another example, as described above, the number of strands removed at each transition point may be one or more than one strands.

The outer surface of the floppy tip 6 and/or body 9 of the guidewire 1 may include friction reducing materials, coatings, surface treatments or lubricious coatings.

FIGS. 5A, 5B, 5C, 5D, 6A, 6B, and 6D illustrate actuators for use with guidewires, such guidewire 1 described above, according to embodiments of the invention. It will be appreciated that the actuators shown in FIGS. 5A-6D may be used with other guidewires as well.

FIGS. 5A, 5B, 5C, and 5D illustrate an exemplary embodiment of an actuator 100. Actuator 100 can be used to achieve a desired guidewire stiffness in a number of ways to address multiple clinical needs that may arise. In one embodiment, actuator 100 can be used to achieve momentary stiffness of guidewire 1. In other words, actuator 100 is used in a manner to achieve a desired guidewire stiffness only while it is attached to the actuation interface 10 of guidewire 1. Alternatively, the actuator 100 may be used to maintain a desired guidewire stiffness even while the actuator is not attached to the actuation interface 10.

The actuator 100 includes a collet cap 101, a collet 102, a rearward clamp 103, a turning clamp knob 104, an actuator slide 105, an actuator body 106, and rings 107-108. The actuator 100 may also include markings 109 on the actuator body 106 to provide feedback to the user corresponding to the guidewire stiffness.

To achieve momentary stiffness, the proximal end 23 of guidewire 1 is inserted into collet cap 101 and advanced into actuator 100 until the guidewire proximal end 23 abuts a guidewire stop positioned proximally of the rearward clamp 103. The rearward actuator land 19 is aligned with rearward clamp 103 such that it is securely held when the rearward clamp 103 is activated by turning clamp knob 104.

In one embodiment, the rearward clamp 103 is a thumb screw inside of the actuator slide 105 of the actuator 100, but other known clamping technologies could be used. This clamping configuration is particularly useful as it will clamp against the slight radial undercut created by the rearward actuator land 19, so very modest tightening force on the clamp knob 104 will prevent axial movement beyond the rearward actuator land 19 when axial force is applied to stiffen, or as will be explained later, release stiffness already being maintained by actuation interface 10.

The clamp knob 104 is then turned to trap rearward actuator land 19 with rearward clamp 103. This securely fixes the outer canister 16 and accordingly the tension cable 3 to the actuator slide 105.

The collet cap 101 is tightened to capture the forward actuator land 15 with jaws of collet 102. Collet 102 is known in the art, and is normally open when the collet cap 101 is loose, allowing insertion and removal of actuation interface 10. Jaws of collet 102 are closed by tightening collet cap 101 to capture forward actuator land 15. This clamping configuration is particularly useful as it circumferentially clamps against the slight radial undercut created by the forward actuator land 15, so a very modest tightening force on the collet cap 101 prevents axial movement beyond the forward actuator land 15 when axial force is applied to stiffen, or as will be explained later, release stiffness already maintained by the actuation interface 10.

Figure 5A:
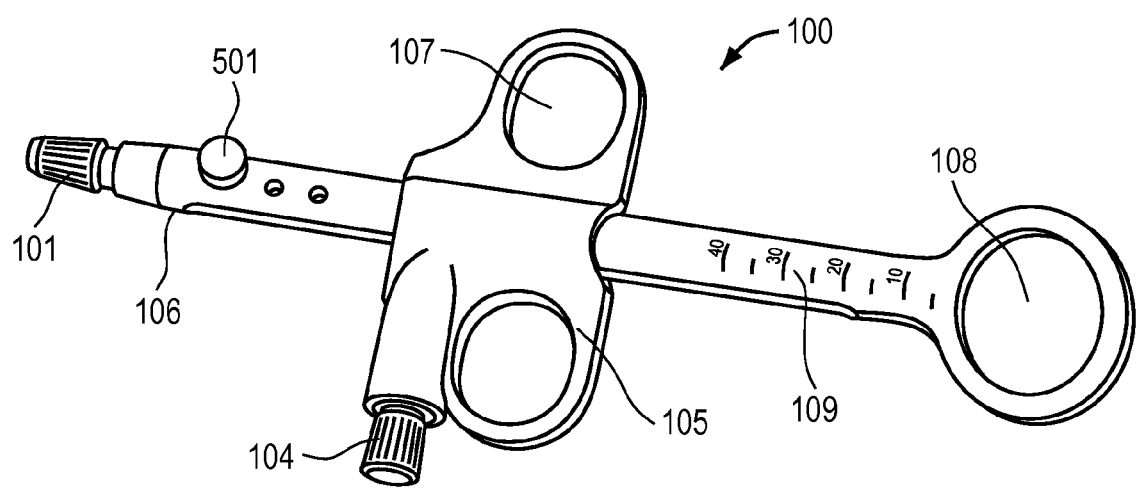
FIGS. 5A-5D are schematic diagrams of an actuator in accordance with one embodiment of the invention.
Figure 5B:
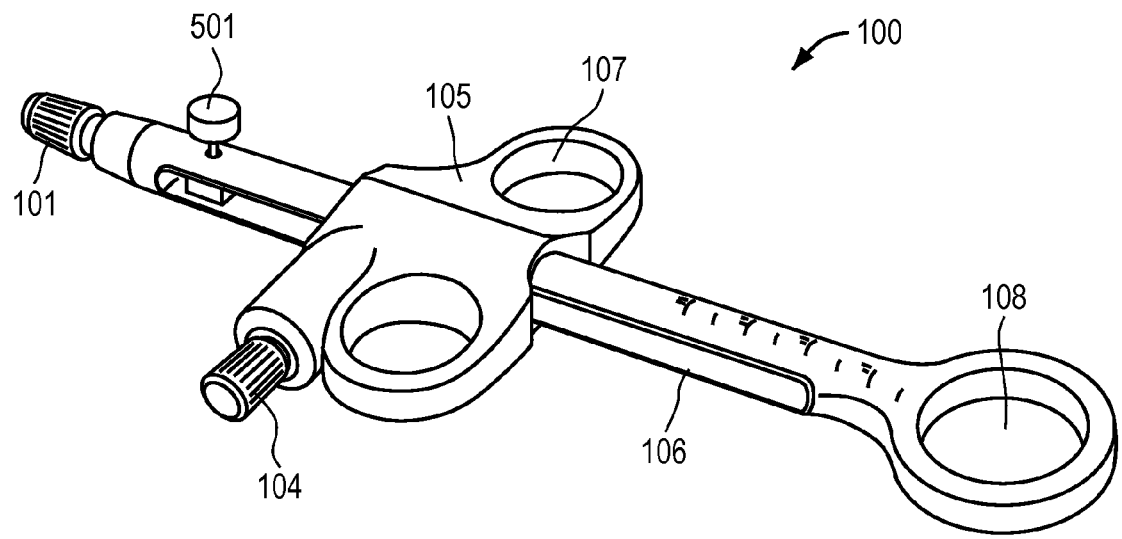
Figure 5C:
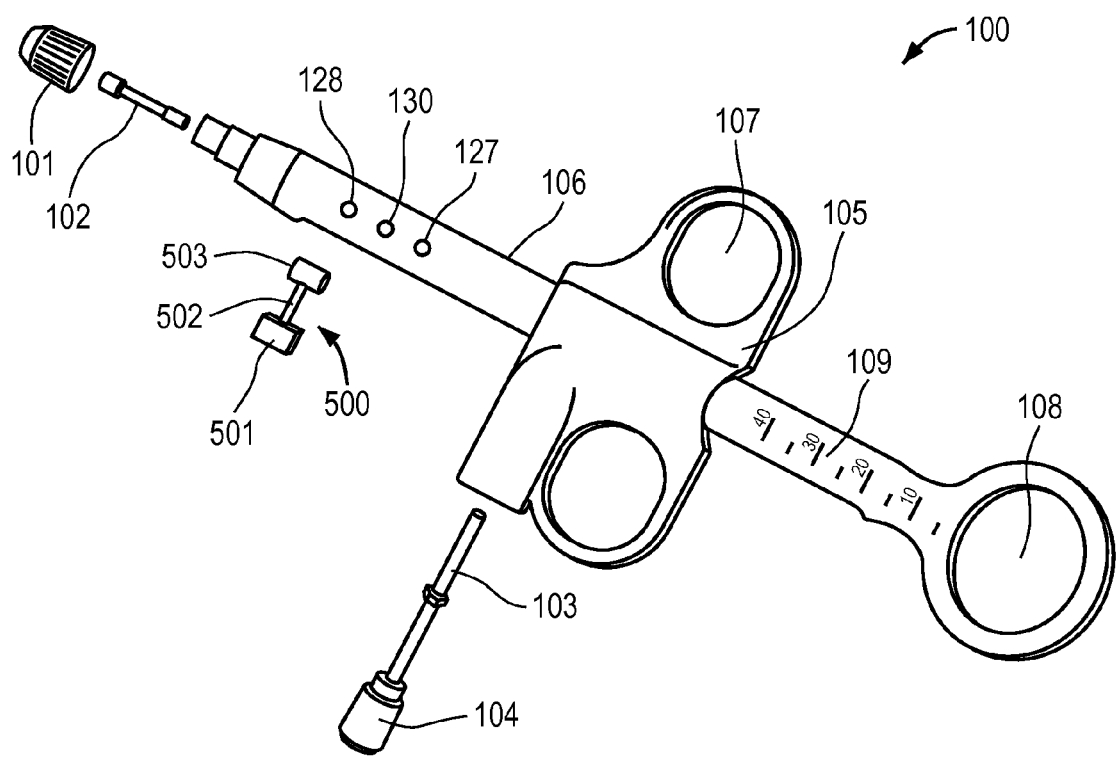
Figure 5D:
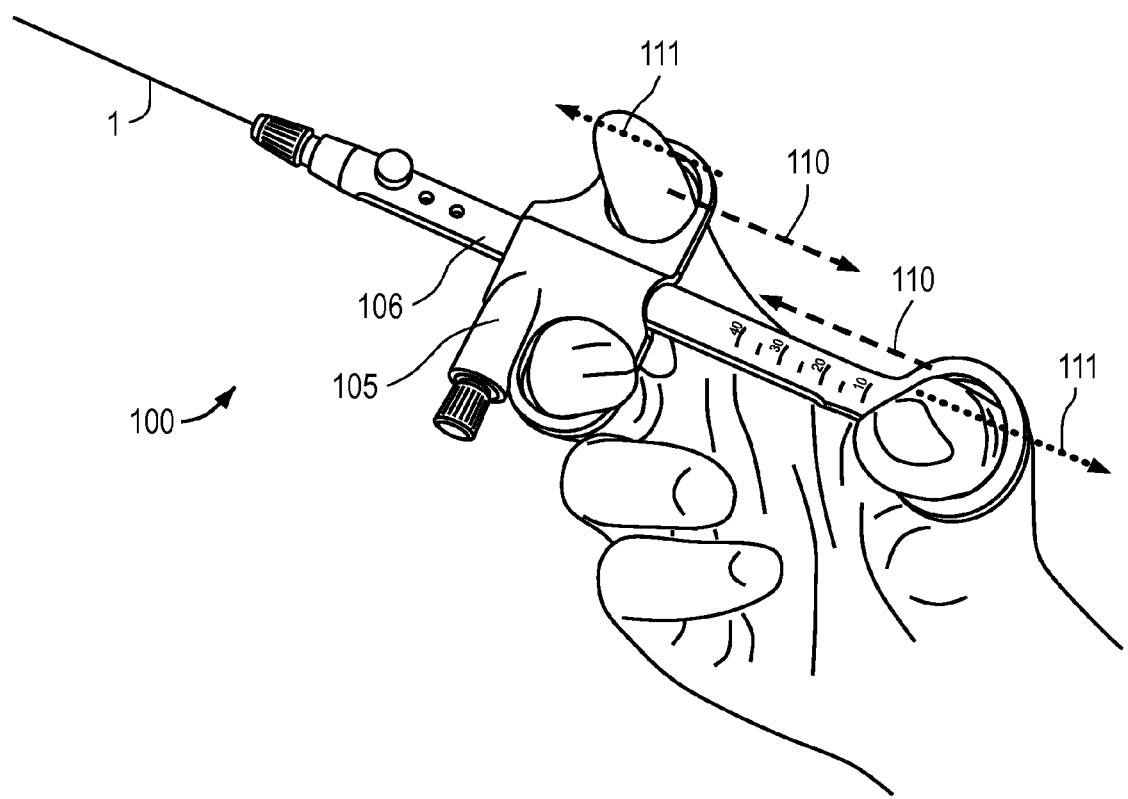

The guidewire stiffness may be selectively increased by the operator by moving the actuator slide 105 proximally with respect to the actuator body 106. Arrows 110 of FIG. 5D illustrate movement of the actuator slide 105 to increase guidewire stiffness. The guidewire stiffness can be selectively decreased by the operator by moving the actuator slide 105 distally with respect to the actuator body 106.

Arrows 111 of FIG. 5D illustrate decreasing the guidewire stiffness. The guidewire stiffness is decreased by pulling the two rings 107 on the actuator slide 105 away from the single ring 108 on the actuator body 106.

In the embodiment illustrated in FIG. 5A-5D, momentary stiffness is achieved as long as the user maintains sufficient force holding rings on the actuator slide and the ring on the actuator body from moving apart. Alternatively, a ratchet or lock mechanism (not shown) could be provided on the actuator body and/or actuator slide such that a user could achieve a desired guidewire stiffness and the actuator could maintain said desired guidewire stiffness. Such a ratchet or lock mechanism may be normally-on, normally-off, alternate-acting, or completely manual.

The actuator 100 may optionally provide the capability to impart a stiffness change to guidewire 1 that is maintained by actuator interface 10 after removing actuator 100 from the guidewire 1. FIG. 1 illustrates an optional crimping tool 500 that resides within actuator body 106 at locations defined by holes 127, 128, and 129 (129 is not shown, but is directly opposite 127) corresponding to crimp locations 27, 28, and 29 respectively. Hole 130 corresponds to a crimp location in between 27 and 28. In other words, crimping tool 500 may be positioned proximally of the jaws of the collet at distances and orientations equal to 27, 28, and 29. Crimping tool 500 includes a crimp knob 501, a threaded pin 502, and a crimp body 503.

Crimp knob 501 is attached to a threaded pin 502 which passes through holes 127, 128, 129, or 130 and is in threaded engagement with a threaded pin receiver in crimp body 503. FIGS. 5A, 5B, and 5D show threaded pin 502 passing through hole 128. A different crimp location can be established by removing threaded pin 502 from crimp body 103 and hole 127, then passing the threaded pin 502 through one of holes 127, 129, or 130 and threading it into the threaded pin receiver in the crimp body 503.

Crimp body 503 includes a guidewire passage hole axially positioned to receive the actuation interface 10 of a guidewire loaded into the actuator. The guidewire passage hole is perpendicular to and in communication with the threaded pin receiver. The portion of the guidewire passage hole aligned with the threaded pin receiver has a diameter only slightly larger than the outer canister 16. In one embodiment, the diameter is about 1%-15% larger, and, in one particular embodiment, the diameter is about 5%-10% larger. This provides the necessary support during crimping and prevents gross distortion of the actuation interface.

The threaded pin 502 can be advanced into the guidewire passage hole a distance sufficient to create deformation 30 on the outer canister 16 of the actuation interface 10. Further advancement of the threaded pin 502 would cause unnecessary canister deformation and may be prevented by a hard stop such as a shoulder on the threaded pin 502 engaging a surface on the crimp body 503. It will be appreciated that during guidewire insertion into or removal from the actuator 100, threaded pin 502 should be positioned within threaded pin receiver such that no part of it extends into the guidewire passage hole.

To impart a maintained stiffness change to guidewire 1, actuator 100 is first used as previously described to achieve a desired stiffness of guidewire 1. While the actuator 100 holds the desired guidewire stiffness, crimping tool 500 is used to create deformation 30 within telescopically mating length 25. Crimp knob 501 is turned until it reaches the hard stop, signaling that deformation 30 has been properly created. The crimp knob 501 is returned to its original position so that no part of the threaded pin 502 extends into the guidewire passage hole. Clamp knob 104 is turned in a direction opposite that used to tighten it, releasing the rearward clamp 103. Collet cap 101 is turned in a direction opposite that used to tighten it, opening the jaws of collet 102. The guidewire 1 can then be removed from actuator 100 while the deformation 30 maintains the stiffness selected by the user.

Subsequent decrease of guidewire stiffness can be accomplished by reinserting actuation interface 10 into actuator 100, tightening jaws of collet 102 by turning collet cap 101, tightening rearward clamp 103 by tuning clamp knob 104, and pulling the two rings 107 on the actuator slide 105 away from the single ring 108 on the actuator body 106. The tension cable force in addition to the additional force from the actuator are sufficient to overcome deformation 30, causing it to yield and allowing distal movement of the outer canister 10 necessary to provide the desired reduction in guidewire stiffness.

Repeated use of previously used crimp locations to maintain guidewire stiffness is possible. Alternatively, an alternate crimp location can be used. These features provide for a nearly infinite selection of maintained guidewire stiffness, and numerous cycles of stiffness application, stiffness maintenance, stiffness release, and reapplication.

Figure 6A:
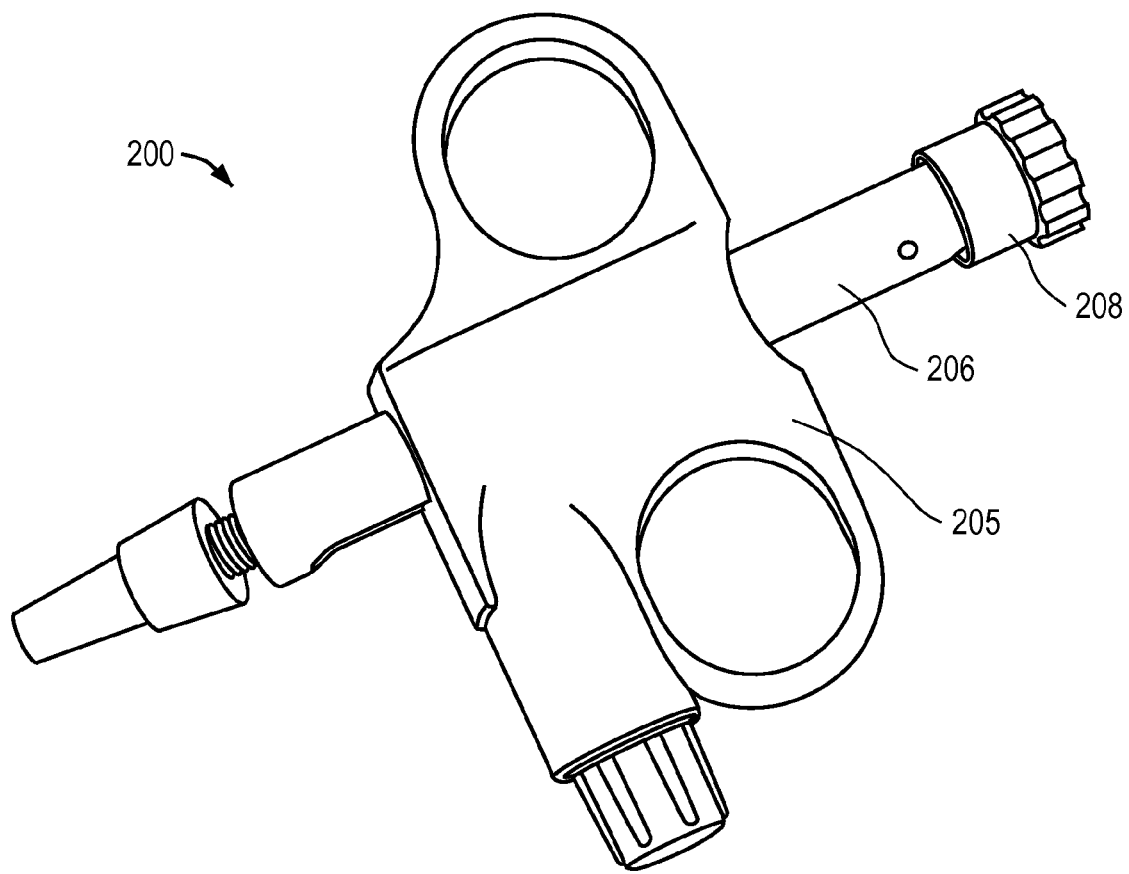
FIGS. 6A-6C are schematic diagrams of an actuator in accordance with one embodiment of the invention.
Figure 6B:
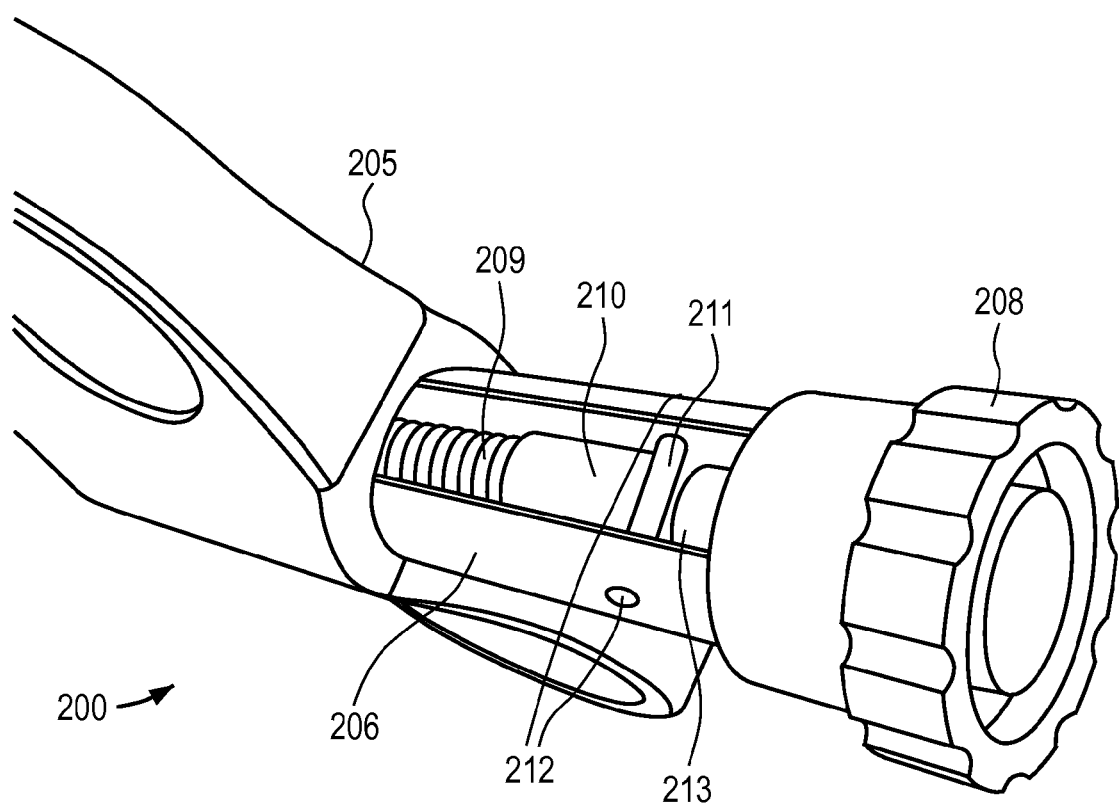

FIGS. 6A and 6B illustrate an actuator 200 according to one embodiment of the invention. Actuator 200 has a mechanism to increase and decrease guidewire stiffness different than the mechanism of actuator 100. Actuator 200 includes an actuator slide 205, an actuator body, a tension knob 208, a tension screw 209, a pin 211 and a follower 214. The tension screw includes a shoulder 210 with a circumferential groove 213.

The tension knob 208 is fixed to a male threaded tension screw 209. The threaded tension screw is in threaded engagement with a mating threaded female follower 214 (not shown). The follower 214 is fixed to and inside of the actuator slide 205. Rotation of the tension knob 208 causes the actuator slide 205 to move proximally or distally with respect to the actuator body 206, which can be rotated until the desired increase or decrease in the stiffness of guidewire 1 is achieved.

The shoulder 210 with a circumferential groove 213 maintains axial stability of the tension screw 209. Actuator body 206 and threaded female follower 214 support tension screw 209 such that it is constrained to one axis. Pin 211 is fixed to actuator body 206 and is tangentially and slidingly received in circumferential groove 213.

Because of the mechanical advantage generated by a screw, actuator 200 allows the user to deliver the high forces required for increased guidewire stiffness with relatively low torque applied to knob 208. As will be explained hereinafter, actuator 200 also allows the user to deliver high forces required to release stiffness already being maintained by the actuation interface 10 with relatively low torque applied to knob 208 in an opposite direction.

Figure 6C:
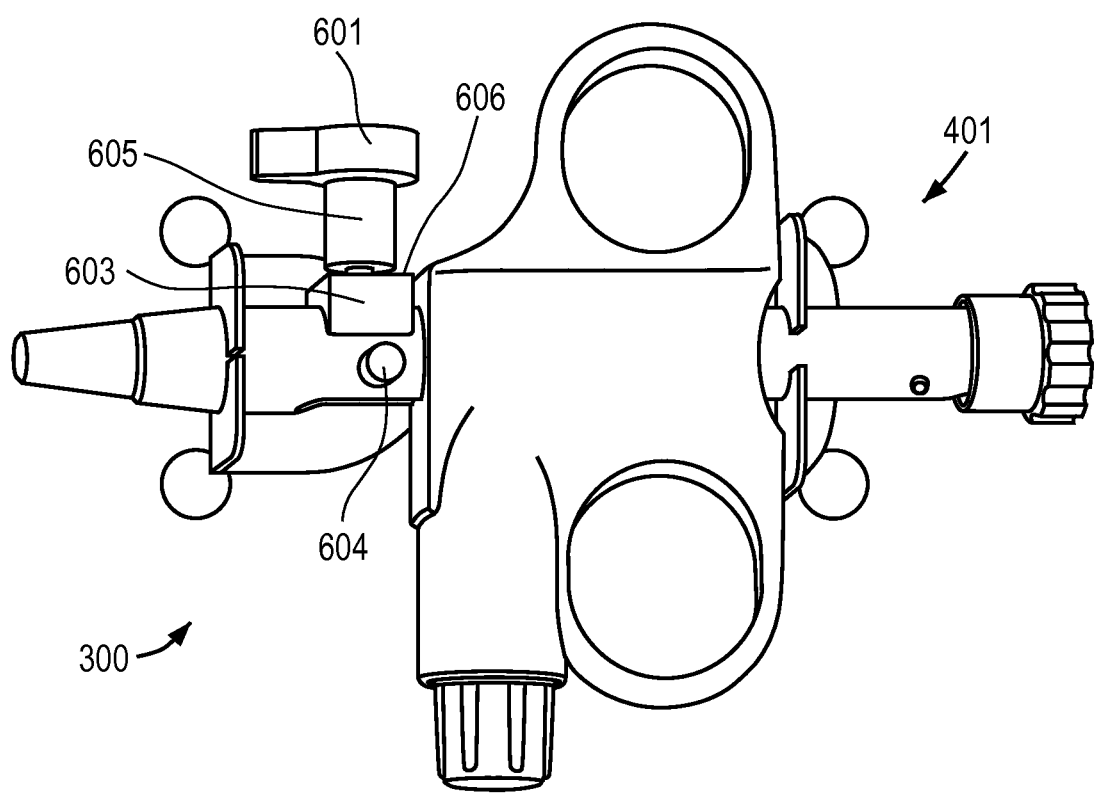

FIG. 6C illustrates actuator 300 according to one embodiment of the invention. Actuator 300 also provides the capability to impart a stiffness change to guidewire 1 that is maintained by actuator interface 10 after removing actuator 300 from the guidewire 1. Actuator 300 is similar to actuator 200, but actuator 300 further includes a crimping tool 600 which resides within actuator body 206 at locations corresponding to crimp locations 27 and 28. The crimping tool includes a crimp knob 601, a threaded pin 602, a crimp body 603, and a spring loaded ball 604. The crimp body 603 includes detents 627 and 628.

Spring loaded ball 604 engages detents 627 and 628 on the side of crimp body 603 at positions that enable the crimping tool 600 to be positioned proximally of the jaws of the collet at distances equal to 27 and 28 respectively. Crimp knob 601 is attached to a threaded pin 602 (similar to threaded pin 502) and is in threaded engagement with threaded pin receiver in crimp body 603. FIG. 6C shows crimping tool 600 with detent 628 engaged by spring loaded ball 604. A different crimp location 27 can be established by pushing the crimping tool 600 proximally until detent 627 is engaged by spring loaded ball 604.

Crimp body 603 includes a guidewire passage hole axially positioned to receive the actuation interface 10 of a guidewire loaded into the actuator. The guidewire passage hole is perpendicular to and communicating with the threaded pin receiver. The portion of the guidewire passage hole aligned with the communicating threaded pin receiver has a diameter only slightly larger than the outer canister 16. In one embodiment, the diameter is about 1%-15% larger, and, in one particular embodiment, the diameter is about 5%-10% larger. This provides the necessary support during crimping and prevents gross distortion of the actuation interface.

The threaded pin 602 can be advanced into the guidewire passage hole a distance sufficient to create deformation 30 on the outer canister 16 of an actuation interface 10 residing within it. Further advancement of the threaded pin 602 causes unnecessary canister deformation and is prevented by a hard stop such as shoulder 605 on the threaded pin 602 engaging surface 606 on the crimp body 603. During guidewire insertion into or removal from the actuator 300, threaded pin 602 should be positioned within threaded pin receiver such that no part of it extends into the guidewire passage hole.

To impart a maintained stiffness change to guidewire 1, actuator 300 is first used as previously described for actuator 200 to achieve a desired stiffness of guidewire 1. While actuator 300 holds the desired guidewire stiffness, crimping tool 600 is used to create deformation 30 within telescopically mating length 25. Crimp knob 601 is turned until shoulder 605 engages surface 606 on the crimp body 603, signaling that deformation 30 has been properly created. The crimp knob 601 is returned to its original position so that no part of the threaded pin 602 extends into the guidewire passage hole. Clamp knob 104 is turned in a direction opposite that used to tighten it, releasing the rearward clamp 103. Collet cap 101 is turned in a direction opposite that used to tighten it, releasing the jaws of collet 102. The guidewire 1 is removed from actuator 300 and deformation 30 maintains the stiffness selected by the user.

Subsequent decrease of guidewire stiffness can be accomplished by reinserting actuation interface 10 into actuator 300, tightening jaws of collet 102 by turning collet cap 101, tightening rearward clamp 103 by tuning clamp knob 104, and turning knob 208 on tension screw 209 in a direction opposite of that used to increase guidewire stiffness. The tension cable force plus the additional force from the actuator are sufficient to overcome deformation 30, causing it to yield and allowing distal movement of the outer canister 10 necessary to provide the desired reduction in guidewire stiffness.

Repeated use of previously used crimp locations to maintain guidewire stiffness is possible. Alternatively, a different crimp location can be used. These features provide for a nearly infinite selection of maintained guidewire stiffness, and numerous cycles of stiffness application, stiffness maintenance, stiffness release, and reapplication.

Figure 7:
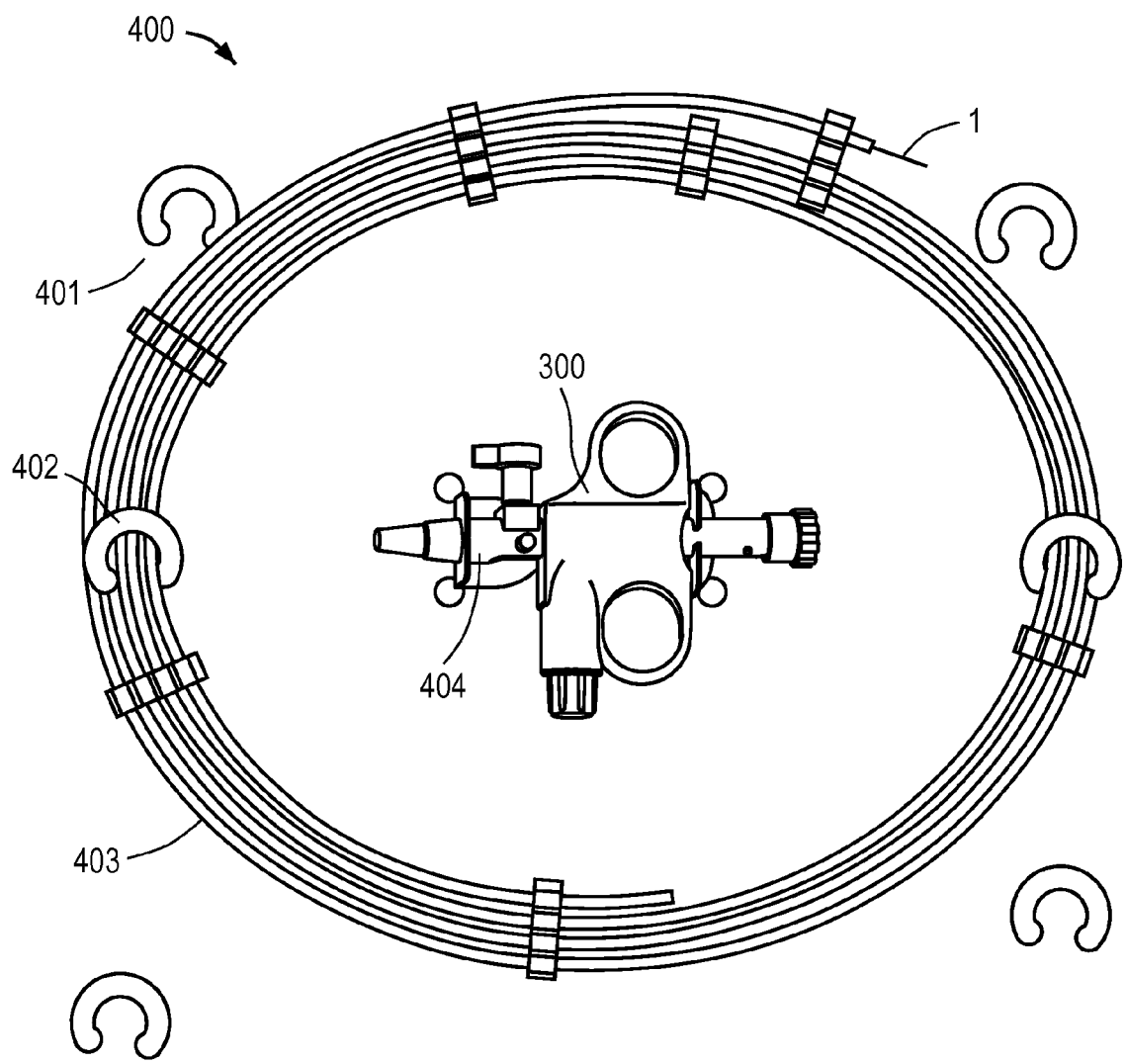
FIG. 7 is a schematic diagram of a kit in accordance with one embodiment of the invention.

FIG. 7 shows a system enabling the methods herein described. FIG. 7 shows a kit 400 according to one embodiment of the invention. Included in kit 400 are guidewire 1 placed within coiled package tubing 403 and attached to packaging card 401 by tabs 402. Also included is actuator 300 attached to packaging card 401 by tabs 404. It will be appreciated that, alternatively, the kit 400 may include actuator 100 or actuator 200. It will also be appreciated that guidewires other than guidewire 1 may be included in the kit 400.

It should be understood that processes and techniques described herein are not inherently related to any particular apparatus and may be implemented by any suitable combination of components. Further, various types of general purpose devices may be used in accordance with the teachings described herein. The present invention has been described in relation to particular examples, which are intended in all respects to be illustrative rather than restrictive. Those skilled in the art will appreciate that many different combinations will be suitable for practicing the present invention.

Moreover, other implementations of the invention will be apparent to those skilled in the art from consideration of the specification and practice of the invention disclosed herein. Various aspects and/or components of the described embodiments may be used singly or in any combination. It is intended that the specification and examples be considered as exemplary only, with a true scope and spirit of the invention being indicated by the following claims.

What is claimed is:

1. A system comprising:
a variable stiffness guidewire including a guidewire body, the guidewire body having a proximal end and a distal end;
an actuator interface at the proximal end of the guidewire body and including an inner canister and an outer canister at least partially telescoping relative to one another;
a tension cable coupled to the outer canister and coupled to the distal end of the guidewire body, the tension cable movable within the inner canister; and
an actuator couplable to the actuator interface and configured to move the outer canister relative to the inner canister to vary the stiffness of the guidewire, wherein the stiffness is adjusted by moving the outer canister distally relative to the inner canister and the actuator includes a crimper configured to maintain the stiffness of the guidewire body at the desired stiffness.

2. The system of claim 1, wherein the actuator interface is configured to increase the stiffness of the guidewire.

3. The system of claim 1, wherein the actuator interface is configured to decrease stiffness of the guidewire.

4. The system of claim 1, wherein the guidewire includes a tip coil and a body coil, and wherein the tip coil is more flexible than the body coil.

5. The system of claim 1, wherein the actuator interface circumferentially clamps the guidewire to maintain the desired stiffness.

6. The system of claim 1, wherein the actuator includes an actuator body and an actuator slide, the actuator slide movable relative to the actuator body to adjust the stiffness of the guidewire via the actuator interface.

7. The system of claim 1, wherein the actuator includes a tension knob coupled to a tension screw.

8. The system of claim 1, wherein the actuator includes markings to identify an amount of stiffness of the guidewire.

9. A variable stiffness guidewire comprising:
a guidewire body, the guidewire body having a proximal end and a distal end;
an actuator interface at the proximal end of the guidewire body and including an inner canister and an outer canister at least partially telescoping relative to one another, wherein the stiffness is adjusted by moving the outer canister distally relative to the inner canister and the actuator interface includes a crimper configured to maintain the stiffness of the guidewire body at the desired stiffness; and
a tension cable coupled to the outer canister, coupled to the distal end of the guidewire body and movable within the inner canister.

10. The variable stiffness guidewire of claim 9, wherein the actuator interface is configured to increase the stiffness of the guidewire.

11. The variable stiffness guidewire of claim 9, wherein the actuator interface is configured to decrease stiffness of the guidewire.

12. The variable stiffness guidewire of claim 9, wherein the guidewire body includes a tip coil and a body coil, and wherein the tip coil is more flexible than the body coil.

13. The variable stiffness guidewire of claim 9, wherein the actuator interface circumferentially clamps the guidewire body to maintain the desired stiffness.

14. A variable stiffness guidewire comprising:
  a guidewire body, the guidewire body having a proximal end and a distal end;
  a floppy tip having a proximal end and a distal end, the proximal end of the floppy tip coupled to the distal end of the guidewire body, the flexibility of the floppy tip being greater at the distal end of the floppy tip than at the proximal end of floppy tip;
  an actuator interface at the proximal end of the guidewire body and including an inner canister and an outer canister at least partially telescoping relative to one another, wherein the stiffness is adjusted by moving the outer canister distally relative to the inner canister and the actuator interface includes a crimper configured to maintain the stiffness of the guidewire body at the desired stiffness; and
  a tension cable coupled to the actuator interface and coupled to the floppy tip.

15. The variable stiffness guidewire of claim 14 wherein the floppy tip includes a plurality of strands and wherein the number of strands at the proximal end is greater than the number of strands at the distal end.

* * * * *